United States Patent [19]

Pay

[11] Patent Number: 5,710,043
[45] Date of Patent: Jan. 20, 1998

[54] IN VITRO CELL CULTURE ASSEMBLY

[75] Inventor: Nicholas George Martin Pay, St Hilaire du Touvet, France

[73] Assignee: Becton Dickinson and Company, Franklin Lakes, N.J.

[21] Appl. No.: 533,983

[22] Filed: Sep. 25, 1995

[51] Int. Cl.⁶ .................................................. C12M 3/06
[52] U.S. Cl. ...................... 435/297.5; 435/305.2
[58] Field of Search ........................... 435/297.1, 297.2, 435/297.5, 288.3–288.5, 305.1–305.4; 422/101, 102; 210/474, 476, 477, 482

[56] References Cited

U.S. PATENT DOCUMENTS

| | | | |
|---|---|---|---|
| 4,296,205 | 10/1981 | Verma | 435/197.5 |
| 4,812,407 | 3/1989 | Buchmann et al. | 435/297.1 |
| 4,871,674 | 10/1989 | Matsui et al. | 435/284 |
| 5,026,649 | 6/1991 | Lyman et al. | 435/284 |
| 5,139,951 | 8/1992 | Butz et al. | |
| 5,215,920 | 6/1993 | Lyman et al. | |
| 5,272,083 | 12/1993 | Butz et al. | |
| 5,366,893 | 11/1994 | Stevens et al. | 435/297.5 |
| 5,409,829 | 4/1995 | Mussi et al. | 435/240.241 |
| 5,466,602 | 11/1995 | Lyman et al. | |

OTHER PUBLICATIONS

Magnum et al., *In Vitro Cell Dev. Biol.* 26:1135–1143 (Dec. 1990), "Co–Culture of Primary Pulmonary Cells to Model Alveolar Injury and Translocation of Protein".

Madara et al., *J. Tissue Cult. Method*, 14:209–216, (1992), "A Simple Approach to Electrical Parameters of Cultured Epithelial Monolayers: Use in Assessing Neutrophil–Epithelial Interactions".

Miller et al., *J. Tissue Cult. Method*, 14:217–224, "Application of Cultured Endothelial Cells of the Brain Microvasculature in the Study of the Blood–Brain Barrier" (1992).

*Science*, 266:564–565 (1995), "Finding Clues About How Embryo Structures Form".

*Primary Examiner*—William H. Beisner
*Attorney, Agent, or Firm*—Arthur D. Dawson; Susan A. Capello

[57] ABSTRACT

An assembly for in vitro culture of cells of the present invention includes a culture vessel with at least one well. The well has an open top, a bottom and a wall with an inside surface. The assembly also includes at least one insert sized for placement within the well. The insert has an outside surface, an open end and a closed end. There is a microporous membrane at the closed end of the insert that closes the end and thereby forms a receptacle within the inset. The assembly further includes provisions for adjustably positioning the insert within the well between a first position where the closed end of the insert is a first distance from said bottom of the well and a second position where the closed end of the insert is a second distance from the well bottom.

1 Claim, 3 Drawing Sheets

IN VITRO CELL CULTURE ASSEMBLY

FIELD OF INVENTION

The present invention generally relates to laboratory cell culture and more particularly to an assembly useful for growing cells or study of tissue development in vitro.

BACKGROUND

Culturing of cells of various types has become a routine process in many laboratories. Cells are cultured to harvest compounds, to test for various sensitivities to potentially toxic compounds and even to provide tissue for grafts. This work generally is a monoculture, i.e., cells of one type are grown in a suitable medium.

More recently, interest has developed in the co-culture of cells. Co-culture of cells involves growing one population of cells in the presence of another population of cells. Co-culture of cells is important for study of inflammation reactions, cell differentiation processes and blood brain permeability studies.

Representative literature reports related to cell co-culture include: Magnum et al., *In Vitro Cell Dev. Biol.* 26:1135–1143 (Dec. 1990), "Co-Culture of Primary Pulmonary Cells to Model Alveolar Injury and Translocation of Protein"; Madara et al., *J. Tissue Cult. Method,* 14:209–216, (1992), "A Simple Approach to Electrical Parameters of Cultured Epithelial Monolayers: Use in Assessing Neutrophil-Epithelial Interactions"; Miller et al., *J. Tissue Cult. Method.,* 14:217–224, "Application of Cultured Endothelial Cells of the Brain Microvasculature in the Study of the Blood-Brain Barrier"; and *Science,* 266:564–565 (1994), "Finding Clues About How Embryo Structures Form." The above referenced articles are cited to provide background regarding the in vitro study of the interaction between one cell type and another.

Miller et al., cited above, describes culturing of cells on solid plastic surfaces and filters or membrane inserts. Miller et al. reports that bovine brain endothelial cells (BBEC) cultured on filters or membrane inserts provide an advantage over BBEC cultured on solid plastic surfaces. This advantage is that cell polarity with respect to metabolism or receptor distribution can be examined. Miller et al. further states that BBEC culture on filters or membrane inserts is required for determining the trans cellular transport or permeability of a compound across the cellular monolayer.

The above referenced *Science* article describes studies on kidney structure development. The article reports Mesenchymal cells co-cultured with cells producing Wnt-1 protein differentiate into kidney structures, including nephron tubular and glomular tissue and reports that this effect is not seen with control cells.

In response to the developing need for devices and equipment to co-culture cells, a co-culture system is disclosed in the commonly assigned U.S. application Ser. No. 08/124,415 by Mussi et al., now U.S. Pat. No. 5,409,829. The disclosure provides a complete self-contained system for preparing a co-culture of cells.

U.S. Pat. No. 5,026,649 to Lyman et al. discloses an insert device that can be utilized to culture and co-culture cells.

U.S. Pat. No. 4,871,674 to Matsui et al. discloses an insert for culturing cells having a porous membrane forming the bottom of a cylinder. The cylinder additionally has provisions for being suspended in a well.

Both the Lyman et al. and the Matsui et al. patents disclose devices that can be used to culture cells on a membrane, but neither is well suited for growing one population of cells on a membrane at varying distances from another population of cells. The cell culture system disclosed in Ser. No. 08/124,415, now U.S. Pat. No. 5,409,829, is well suited to culture cells on both sides of a membrane, but the distance is fixed and the system requires a series of manipulations that may be time consuming for screening studies where multiple co-cultures are being developed.

In all of the apparatus and techniques described in the cited references and patents, when a cell culture insert with a porous membrane is suspended in a vessel for a cell culture, the distance between the porous membrane the bottom of the suspending vessel is fixed and constant. In some applications in the study and development of organ cells where structures develop, e.g., kidney cultures with nephron tubules and glomular tissue, it is often desired to see structural differentiation develop. There is a need for an apparatus that allows the researcher the ability to adjust the distance between the bottom of the well of the vessel and the insert. Another benefit to having an adjustable distance between the insert and the well bottom is that a researcher can compensate for varying amounts of culture media and specimen volumes. An apparatus which fulfills this need is described below.

SUMMARY

An assembly for in vitro culture of cells of the present invention includes a culture vessel with at least one well therein. The well has an open top, a bottom and a wall with an inside surface. The assembly also includes at least one insert sized for placement within the well. The insert has an outside surface, an open end and a closed end. There is a microporous membrane at the closed end of the insert that closes the end and thus forms a receptacle within the insert. The insert is adjustably positionable within the well to vary the distance between the closed end of the insert and the bottom of the well.

The assembly of the present invention is particularly useful for studies of structure differentiation in embryo cells into organ cells as well as in culture of models for tumors and tissue penetration. Currently available culture assemblies with an insert suspended in a well have a fixed distance between the membrane on the closed bottom of the insert and the bottom of the vessel. In many cases, the amount of culture media and cell suspension available is insufficient to provide the desired contact between the medium and the insert membrane without dilution of the suspension. In other cases as the culture develops, effects of tissue differentiation are not seen as the distance between the membrane and the growing cells in the vessel becomes too small for structures such as nephron tubules and glomerular tissue to properly differentiate. The assembly of the present invention allows the distance between the cell insert and the culture vessel to be varied, thus enabling a researcher to optimize the distance between the insert and the vessel bottom for a particular experiment.

DETAILED DESCRIPTION

Figure 1:
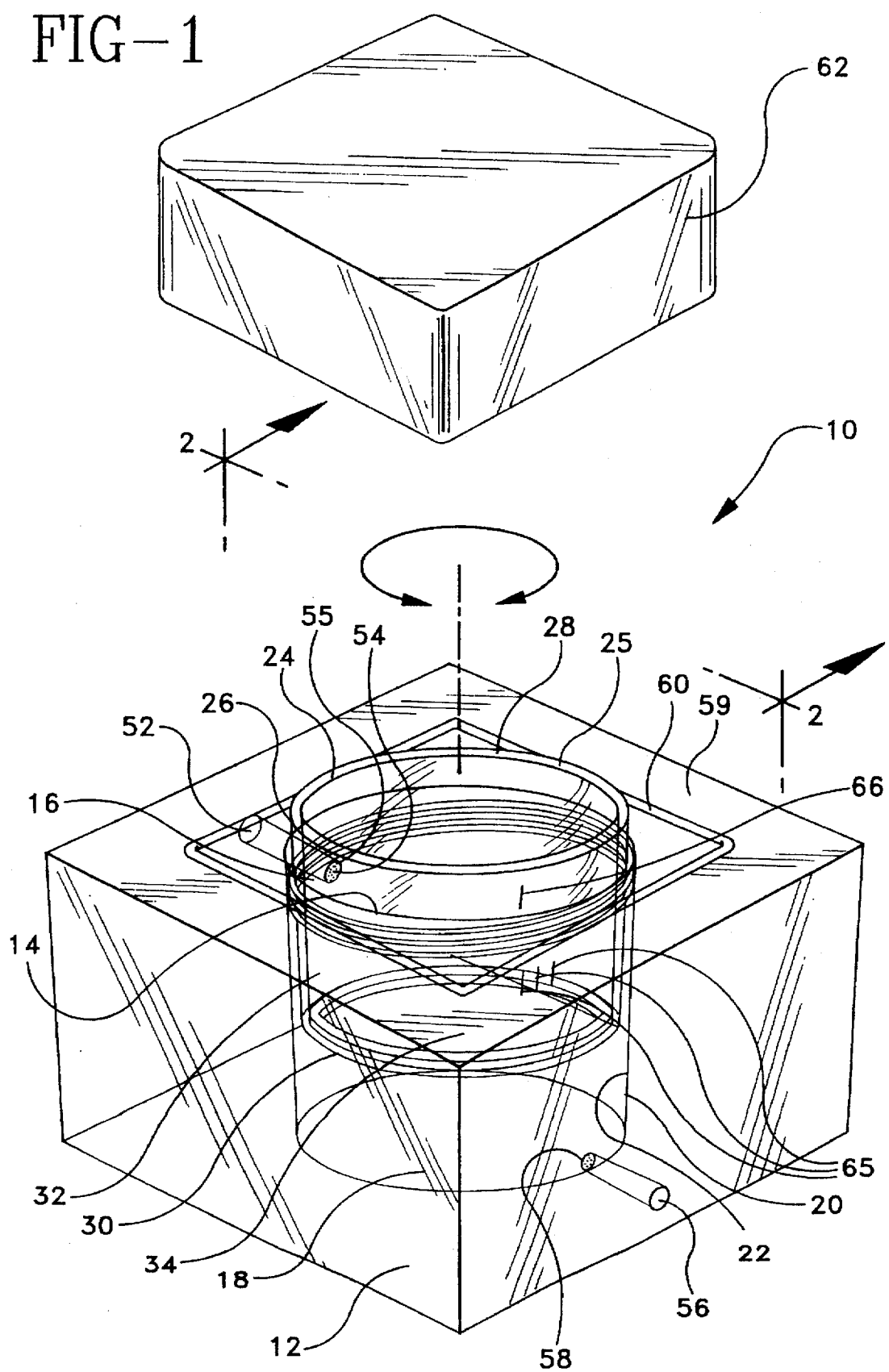
FIG. 1 is a partially exploded perspective view of a cell culture assembly of the present invention.

While this invention is satisfied by embodiments in many different forms, there is shown in the drawings and described herein detail preferred embodiments of the invention with the understanding that the present disclosure is to be considered exemplary of the principles of the invention and is not intended to limit the invention to the embodiments illustrated. The scope of the invention is to be measured by the appended claims and their equivalents.

Figure 2:
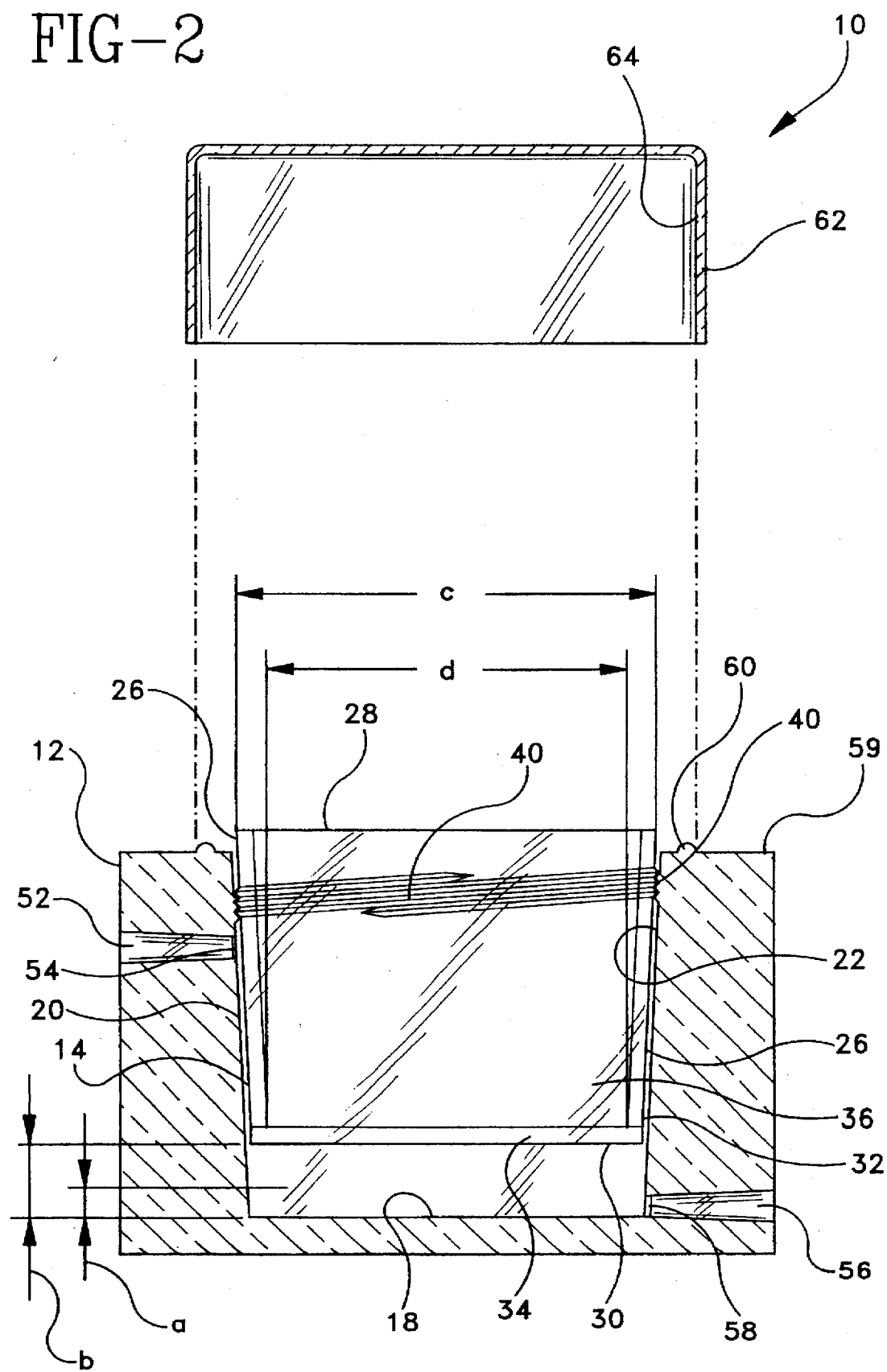
FIG. 2 is a cross-sectional view of the assembly of FIG. 1 taken along the line 2—2.

As shown in FIGS. 1 and 2, an assembly 10 of the present invention useful for in vitro culture of cells includes a culture vessel 12 with at least one well 14 therein. Well 14 has an open top 16, a bottom 18 and a wall 20 with an inside surface 22. Assembly 10 includes at least one insert 24, preferably tubular in shape, that is sized for placement within well 14. Insert 24 has a sidewall 25 with an outside surface 26, an open end 28, a closed end 30 and a cavity 32 from open end 28 to closed end 30. Closed end 30 is closed by microporous membrane 34 forming a receptacle 36 within the insert. Insert 24 is positioned adjustably within well 14 between a first position where closed end 30 is positioned a first distance "a" from bottom 18 of the well and a second position where closed end 30 is positioned a second distance "b" from bottom 18 of the well. In this description, for convenience, assembly 10 is shown as having only one well. Multi-well assemblies with like numbers of inserts are considered to be within the scope of the present invention.

Preferably, insert 24 is positioned adjustably within well 14 by conjugate threads 40 on inside surface 22 of the well and on outside surface 26 of the insert. Preferred threads 40 facilitate adjustable positioning of insert 24 within well 14 by rotation of the insert with respect to vessel 12. In the preferred embodiment, insert 24 is adjustable so that closed end 30 is between about 0.5 mm to about 1.5 cm from bottom 18 of the well. Most preferably insert 24 is adjustable so that membrane 34 is positioned between about 5 mm to about 50 mm from bottom 18 of the well.

Culture vessel 12 preferably includes at least one port for providing access to well 14. More preferably, vessel 12 includes an upper port 52 serving as a vent having a filter 54 to well 14 and a lower port 56 with a pierceable, preferably self-sealing, septum 58 positioned to allow withdrawal of substantially all of an amount of liquid from well 14. Preferably, filter 54 allows atmospheric interchange between the outside environment and well 14 while it substantially prevents passage of microorganisms into well 14. Lower port 56 allows a researcher to add or remove liquid culture medium from well 14 without substantially disrupting the cell growth. The medium may be replaced or changed using the lower port. The presence of port 52, allows the interchange of gases between well 14 and the chamber and atmospherically compensates for addition and withdrawal of fluid medium through lower port 56. Culture vessel 12 has a top 59 that preferably includes an upward rib 60 to provide a barrier that substantially prevents liquid spilled on the top surface from flowing into well 14. The preferred assembly includes a lid 62 sized to cover well 14 and provide clearance for insert 24 when it is positioned in the well. When lid 62 is positioned on top 59, it preferably covers rib 60 so that any condensation forming on an inside surface 64 of the lid and running down onto top 59 is substantially channeled away from well 14. Preferably, lid 62 and rib 60 substantially prevent microorganisms from entering well 14.

Top 59 preferably includes a plurality of markings 65 that when aligned with a mark 66 on insert 24 provide an indication of the distance of porous membrane 34 from well bottom 18. Preferably, mark 66 is aligned with one of markings 65 when insert is in the first position and a second of markings 65 when the insert is in the second position with respect to well bottom 18 thus providing the researcher with an indication of the distance between membrane 34 and well bottom 18.

Culture vessel 12 is preferably formed from thermoplastic resin substantially free from materials extractable by aqueous cell culture media. Suitable materials for forming culture vessel 12 include, but are not limited to, polystyrene, polyethylene terephthalate, polyethylene terephthalate nitrile and the like.

While insert 24 preferably is shaped as a frustum of a cone with a first diameter "c" at open end 28 and a second diameter "d" at closed end 30, other shapes are considered to be within the scope of the invention. Diameter "c" is preferably larger than diameter "d." Sidewall 25 of insert 24 preferably is substantially rigid and formed from thermoplastic resin. Suitable thermoplastic resins include, but are not limited to, polyethylene terephthalate, polyethylene, polystyrene, polycarbonate and the like. Microporous membrane 34 is preferably formed from materials such as polyethylene terephthalate, polycarbonate and the like. Membrane 34 has a multiplicity of open pores therethrough preferably sized between about 0.2 to about 40.0 microns with a pore density between about $0.1 \times 10^6$ to about $10.0 \times 10^8$ pores per square centimeter.

The cell culture assembly of the present invention allows a researcher to culture one population of cells above the membrane in the receptacle formed by the porous membrane in an environment of close proximity to another population of cells on the bottom of well 14. As the culture develops, the variable position of the insert in the well allows the repositioning of the insert either to maintain the original spacing relationship as the numbers of cells increases, or to increase the distance between the first and second populations of cells to encourage structure development in the system. Recent articles by K. Nowak and J. Travis in Science:266, pp.567–568 and 568–570 (1994), respectively, describe potential functions of cellular communication in organ formation in embryos and in neuron development. The assembly of the present invention, by having a variable distance between the porous membrane and the well bottom, provides a researcher with the ability to study distance effects on the cellular development. Preferred assembly 10, with ports 52 and 56, also allows the researcher to control the environment of the cell populations by refreshing or changing the culture medium in the well without disruption of the cells as well as adjusting the spacing between the insert and the vessel bottom. The presence of lower port 56 allows withdrawal of samples of the liquid medium from the well without disruption of the growing cells In most available cell culture assemblies, as referenced above, a researcher must enter the well with a pipet from the open top to withdraw a sample or to change the culture medium. The use of a pipet may disrupt the growing cells.

Cell culture is also used in laboratory procedures on a specimen drawn from a patient or a laboratory animal. These in vivo specimens are not necessarily always the correct volume for fixed distance cell culture apparatus. Preferred apparatus 10 allows the laboratory worker to compensate easily for variable sample size by adjusting the distance between porous membrane 34 on the insert and bottom 18 of the well. Previously, the laboratory worker would need to make up the volume by diluting the suspension with medium which may distort the results of the procedure.

Figure 3:
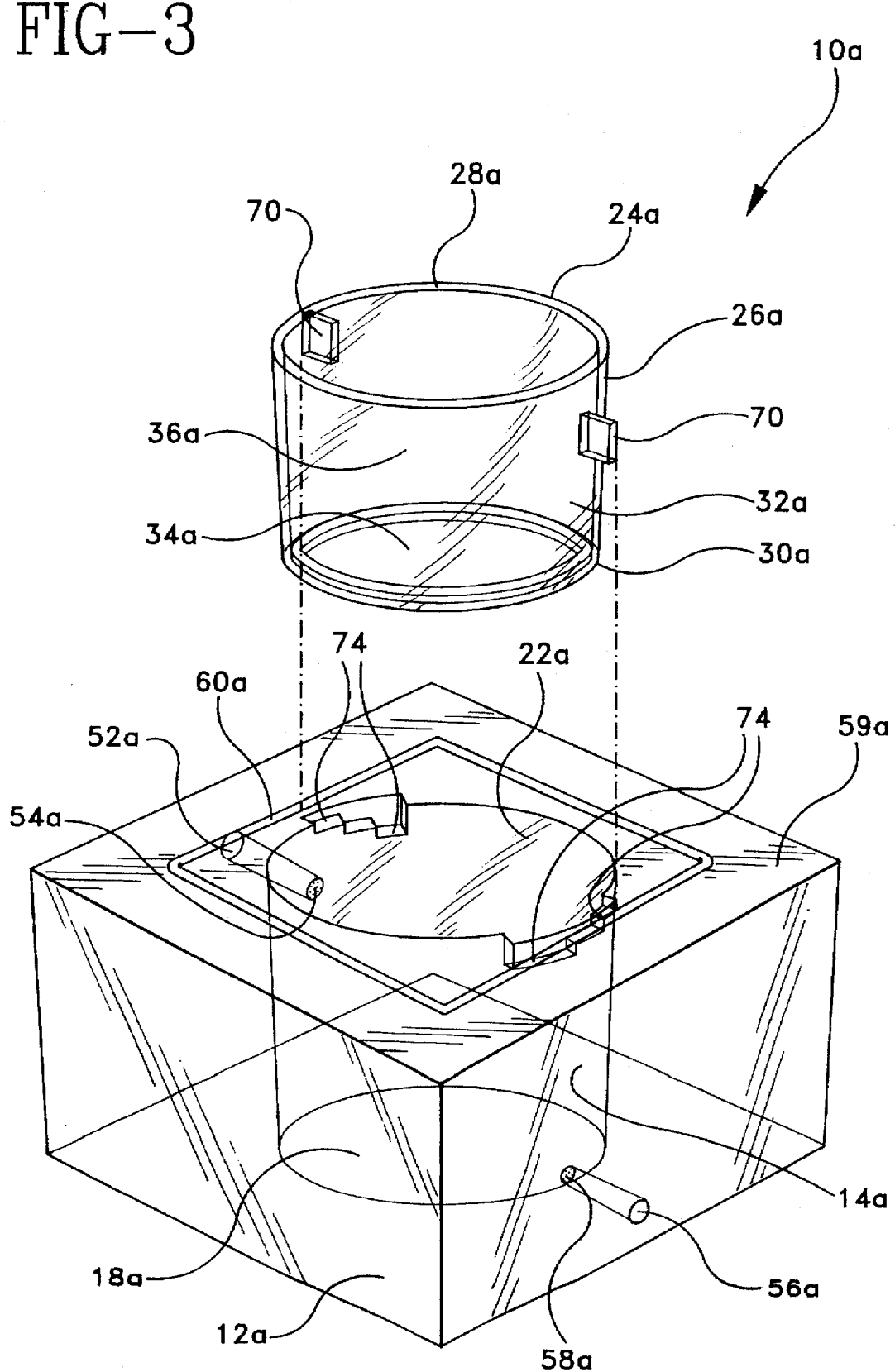
FIG. 3 is an exploded perspective view of an alternative embodiment of the cell culture assembly of FIG. 1.

Referring to FIG. 3, an alternative embodiment of the assembly of the present invention is illustrated. In this embodiment, some elements of the assembly are substantially similar to those illustrated in FIGS. 1 and 2, Accordingly, substantially similar components that perform substantially similar functions are numbered similarly to those of FIGS. 1 and 2 except that a suffix "a" is used to identify those components in FIG. 3.

In this embodiment, outside surface 26a of insert 24a has at least two outward projections 70 positioned to engage a plurality of steps 74 in inside surface 22a of well 14a in a cam/cam follower relation. Steps 74 are arranged at several distances from well bottom 18a thus allowing insert 24a to be variably positioned in well 14a between the first position and the second position above well bottom 18a. Insert 24a is adjustably positioned by rotating insert 24a with respect to vessel 12a to place projections 70 on steps 74 to provide the desired separation between porous membrane 34a and vessel bottom 18a.

The assembly of the present invention is particularly useful for studies of structure differentiation in embryo cells into organs and in culture of models for tumors and tissue penetration. The assembly of the present invention allows the distance between the cell insert and the culture vessel to be varied, thus enabling a researcher easily to optimize the distance for a particular experiment or to study the effects of distance on the cellular communication and transport.

What is claimed is:

1. An assembly for in vitro culture of cells comprising:

a culture vessel having at least one well therein, said well having an open top, a bottom and a wall having an inside surface;

at least one insert sized for placement within said well, said insert having an outside surface, an open end, a closed end, said closed end being closed by a microporous membrane forming a receptacle within said insert;

positioning means for adjustably positioning said insert within said well so that a distance between said closed end of said insert and said bottom of said well is selectively variable, wherein said positioning means comprises at least one outward projection on said outside surface of said insert and a plurality of steps projecting inwardly from said inside surface of said well at increasing distances from said bottom of said well, said projection and said steps disposed in a cam/cam follower relation for adjustably positioning said insert in said well by placing said projection on said steps.

* * * * *